US00PP24582P2

(12) United States Plant Patent
Zaiger et al.

(10) Patent No.: US PP24,582 P2
(45) Date of Patent: Jul. 1, 2014

(54) PEACH TREE NAMED 'SUMMER FIRE'

(50) Latin Name: *Prunus persica*
Varietal Denomination: SUMMER FIRE

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 41 days.

(21) Appl. No.: 13/694,504

(22) Filed: Dec. 7, 2012

(51) Int. Cl.
*A01H 5/00* (2006.01)

(52) U.S. Cl.
USPC ..... Plt./197

(58) Field of Classification Search
CPC .. A01H 5/0868; A01H 5/0856; A01H 5/0837
USPC ..... Plt./197
See application file for complete search history.

*Primary Examiner* — Kent L Bell

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Fruit with a high degree of attractive red skin color.
3. Heavy and regular production of very large size fruit.
4. Firm, yellow fleshed fruit with very good flavor and eating quality.
5. Fruit being relatively uniform in size throughout the tree.

1 Drawing Sheet

Botanical designation: *Prunus persica.*
Variety denomination: 'SUMMER FIRE'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

2. Prior varieties

Among the existing varieties of peach trees, which are known to us, and mentioned herein, 'Zee Lady' Peach (U.S. Plant Pat. No. 5,832), 'Zee Diamond' Peach (U.S. Plant Pat. No. 9,673), 'Vista' Peach (U.S. Plant Pat. No. 9,549), 'Sunnirich' Peach (U.S. Plant Pat. No. 21,567) and our proprietary non-patented peach seedling selection '175LE265'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between 'Zee Lady' Peach (U.S. Plant Pat. No. 5,832) and our proprietary non-patented peach seedling selection '175LE265'. The pollen parent '175LE265' peach (non-patented) originated as a first generation cross between 'Zee Diamond' Peach (U.S. Plant Pat. No. 9,673) and 'Vista' Peach (U.S. Plant Pat. No. 9,549). A large group of these first generation crosses were planted and maintained on their own root system, during which time we recognized the desirable fruit and tree characteristics of the present seedling and selected it in 1999 for further asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree is of large size, vigorous, upright growth and a regular and productive bearer of very large size, firm, yellow flesh, semi-clingstone fruit with good handling and shipping quality. The fruit is further characterized by having moderately juicy flesh, attractive red skin color and having very good eating quality. In comparison to its seed parent 'Zee Lady' Peach (U.S. Plant Pat. No. 5,832) the fruit of the new variety is semi-clingstone compared to freestone and is approximately 17 days earlier in maturity. In comparison to its pollen parent '175LE265' peach (non-patented) the fruit of the new variety is larger in size and is approximately 30 days later in maturity. In comparison to the commercial variety 'Sunnirich' Peach (U.S. Plant Pat. No. 21,567) the fruit of the new variety is approximately 8 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 12 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 12 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, growth of 1.5 to 2 meters in height the first growing season. Varies slightly with soil type, fertility and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size. Number of fruit set varies with climatic conditions during blooming period.

*Bearer*.—Regular, has had an adequate fruit set 11 consecutive years. No alternate bearing observed.

*Fertility*.—Self fertile.

*Density*.—Medium dense, usually pruned to vase shape to increase air movement and sunlight to the center of the tree to enhance fruit color and health of fruit wood.

*Hardiness*.—Hardy in all stone fruit growing areas of California. Tree grown in USDA Hardiness Zone 9. Winter chilling requirement approximately 900 hours at or below 45° F.

Trunk:

*Size*.—Medium. Average circumference 40.6 cm at 20.3 cm above ground on a 12 year old tree.

*Stocky*.—Medium stocky.

*Texture*.—Medium shaggy, roughness increases with age.

*Color*.—Varies from 2.5Y 7/2 to 2.5Y 6/2.

Branches:

*Size*.—Medium. Average circumference 14.7 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 44 in a 25.8 sq cm section. Average length 4.0 mm. Average width 1.6 mm. Color varies from 7.5YR 6/8 to 7.5YR 5/10.

*Color*.—New growth varies from 2.5GY 6/6 to 2.5GY 5/8 with 10R 4/4 where exposed to the sun. Mature growth varies from 7.5YR 3/4 to 7.5YR 2/4, varies with age of growth.

Leaves:

*Size*.—Large. Average length 189.7 mm. Average width 51.2 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, small ridges created by midrib and pinnate venation. Both upper and lower surfaces glabrous.

*Petiole*.—Average length 11.6 mm. Average width 1.7 mm. Longitudinally grooved. Surface — glabrous. Color varies from 2.5GY 6/6 to 2.5GY 6/8.

*Glands*.—Reniform. Size — large. Average length 1.4 mm. Average diameter 0.8 mm. Average number 2, varies from 2 to 3. Located primarily on base of leaf blade, upper portion of petiole.

*Stipules*.—None present.

*Color*.—Upper surface varies from 2.5GY 3/2 to 5GY 2/4. Lower surface varies from 5GY 5/2 to 5GY 4/2. Midvein color varies from 2.5GY 7/2 to 2.5GY 7/4.

Flower buds:

*Size*.—Large. Average length 19.1 mm. Average diameter 10.5 mm.

*Hardiness*.—Hardy with respect to California winters.

*Form*.—Conical, becoming elongated before opening.

*Pedicel*.—Average length 5.2 mm. Average width 1.1 mm. Color varies from 2.5GY 6/8 to 5GY 5/6.

*Color*.—Varies from 7.5RP 6/10 to 7.5RP 5/14.

Flowers:

*Blooming period*.—Date of First Bloom Mar. 3, 2012. Date of Petal Fall Mar. 14, 2012, varies slightly with climatic conditions.

*Size*.—Small to medium. Average height 19.9 mm. Average diameter 25.1 mm.

*Petals*.—Normally 5, alternately arranged to sepals. Size — medium. Average length 15.5 mm. Average width 13.5 mm. Form — obovate, cupped. Margin — sinuate. Both upper and lower surfaces glabrous. Color varies from 7.5RP 6/10 to 7.5RP 6/12, fades with age of flower.

*Sepals*.—Normally 5, alternately arranged to petals. Size — medium to large. Average length 6.3 mm. Average width 5.1 mm. Shape — ovate. Margin-entire. Surface — upper surface glabrous, lower surface pubescent. Color — upper surface varies from 2.5GY 6/6 to 2.5GY 5/6. Lower surface varies from 2.5GY 6/6 to 7.5R 3/4.

*Stamens*.—Average number per flower 37, varies from 32 to 40. Average filament length 16.2 mm. Filament color varies from N 9.5/(white) to 7.5RP 5/8. Anther color varies from 7.5R 4/10 to 5Y 8/8.

*Pollen*.—Self-fertile. Color varies from 5Y 8.5/10 to 5Y 8/8.

*Pistil*.—Normally 1. Surface — pubescent. Average length 18.9 mm. Position of stigma average of 1.2 mm below anthers. Color varies from 10Y 7/4 to 2.5GY 7/6.

*Fragrance*.—Wanting.
*Color*.—Varies from 7.5RP 6/10 to 7.5RP 6/12.
*Number flowers per flower bud*.—Normally one.
*Pedicel*.—Average length 5.6 mm. Average width 1.2 mm. Color varies from 2.5GY 5/8 to 5GY 5/8.

Fruit:
*Maturity when described*.—Firm ripe.
*Date of first picking*.—Jul. 9, 2012.
*Date of last picking*.—Jul. 16, 2012, varies slightly with climatic conditions.
*Size*.—Very large. Average diameter axially 71.0 mm. Average transversely in suture plane 75.2 mm. Average weight 252.8 gram, varies slightly with fertility of the soil, amount of thinning and climatic conditions.
*Form*.—Globose.
*Suture*.—Shallow, extends from base to apex.
*Ventral surface*.—Nearly smooth, extends from base to apex.
*Apex*.—Nearly rounded.
*Base*.—Retuse.
*Stem cavity*.—Rounded to slightly elongated in suture plane. Average depth 4.3 mm. Average diameter 16.0 mm.

Stem:
*Size*.—Small to medium. Average length 9.2 mm. Average diameter 3.4 mm.
*Color*.—Varies from 2.5GY 5/6 to 5GY 6/6.

Flesh:
*Ripens*.—Evenly.
*Texture*.—Firm, meaty.
*Fibers*.—Few, small, tender.
*Firmness*.—Good, holds firm on tree 10 days after maturity (shipping ripe).
*Aroma*.—Moderate.
*Amydgalin*.—Undetected.
*Eating quality*.—Very good.
*Flavor*.—Very good.
*Juice*.—Moderate amount, enhances flavor.
*Brix*.—Average Brix 10.5°, varies slightly with amount of fruit per tree and climatic conditions.
*Color*.—Varies from 10YR 7/8 to 10YR 7/10, slight bleeding into flesh — 5R 3/10.
*Pit cavity*.—Average length 37.1 mm. Average width 29.4 mm. Average depth 11.8 mm. Color varies from 5R 3/10 to 7.5R 3/10.

Skin:
*Thickness*.—Medium.
*Surface*.—Smooth.
*Pubescence*.—Moderate amount.
*Tendency to crack*.—None.
*Color*.—Ground color varies from 2.5Y 8.5/8 to 2.5Y 8/6. Overspread with 5R 4/8 to 7.5R 3/8.
*Tenacity*.—Tenacious to flesh.
*Astringency*.—None.

Stone:
*Type*.—Semi-clingstone.
*Size*.—Large. Average length 36.1 mm. Average width 28.4 mm. Average thickness 21.6 mm.
*Form*.—Ovoid.
*Base*.—Flat.
*Apex*.—Rounded.
*Surface*.—Pitted throughout, pits vary from rounded to elongated.
*Sides*.—Unequal, with one side extending further from suture plane.
*Ridges*.—Small ridges extending from base toward apex.
*Tendency to split*.—None.
*Color*.—Varies from 5R 3/6 to 7.5R 2/8 when dry.

Kernel:
*Size*.—Large. Average length 18.8 mm. Average width 12.5 mm. Average depth 6.4 mm.
*Form*.—Ovoid.
*Viability*.—Viable, complete embryo development.
*Skin color*.—Varies from 10YR 6/8 to 2.5Y 9/4.

Use:
*Dessert*.—Market — local and long distance.

Keeping quality: Good, held firm in cold storage at 38° to 42° F. for 2 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

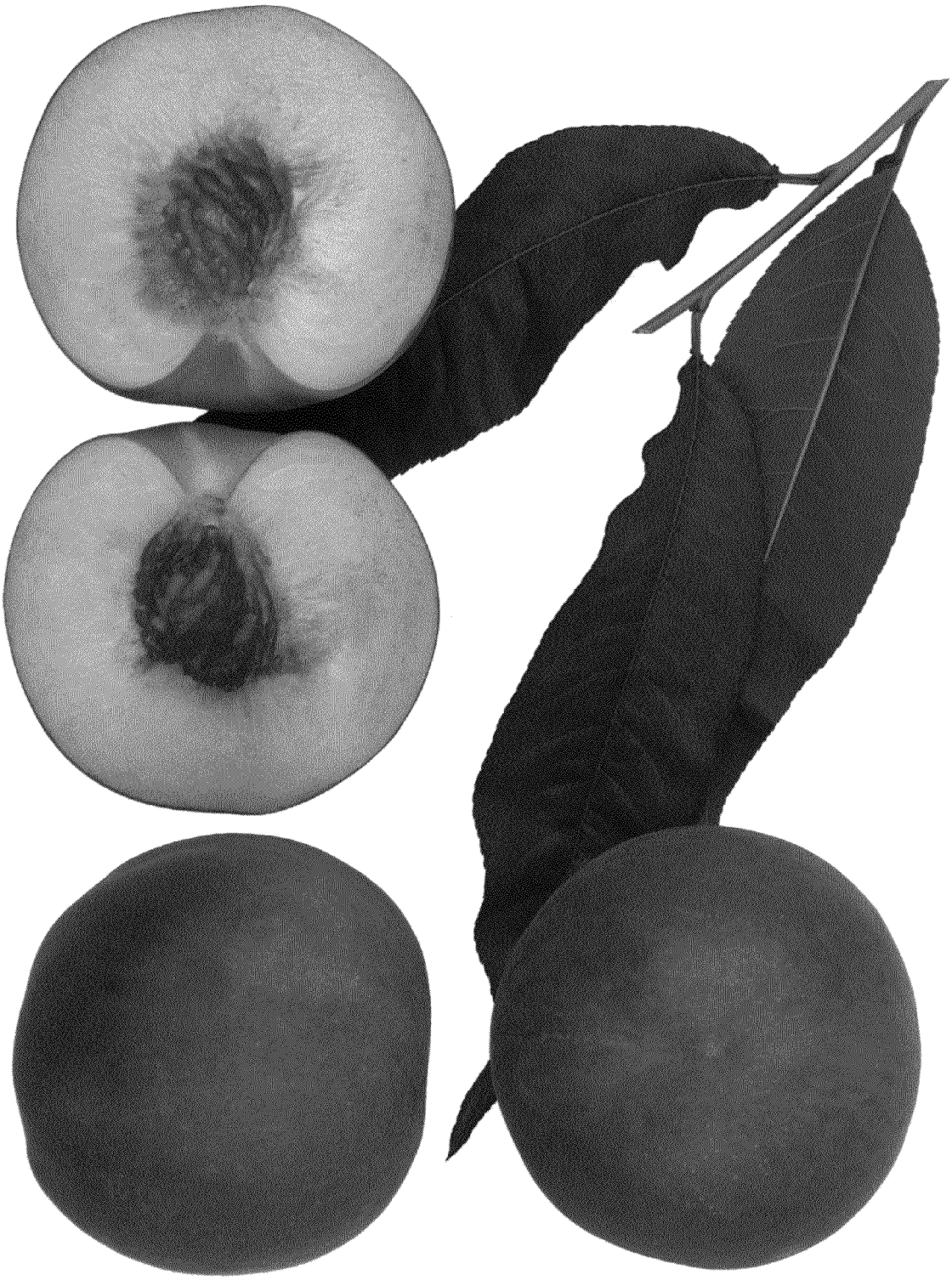

* * * * *